United States Patent [19]

Kitchen et al.

[11] Patent Number: 4,569,236

[45] Date of Patent: Feb. 11, 1986

[54] BIOLOGICAL FLUID SAMPLER

[75] Inventors: Barry J. Kitchen; Clark Annand; James L. Jamieson; Ronald J. Marschke, all of Brisbane, Australia

[73] Assignee: Michael John Ahern, Brisbane, Australia

[21] Appl. No.: 500,866

[22] Filed: Jun. 3, 1983

[30] Foreign Application Priority Data

Jun. 8, 1982 [AU] Australia ................ PF4352

[51] Int. Cl.$^4$ .............................................. G01N 1/10
[52] U.S. Cl. ................... 73/863.31; 73/863.86; 137/625.19; 128/762
[58] Field of Search .......... 73/863.31, 863.33, 863.81, 73/863.86; 137/625.19; 128/762, 760; 604/32, 248

[56] References Cited

U.S. PATENT DOCUMENTS

| | | | |
|---|---|---|---|
| 159,960 | 2/1875 | Pfund | 137/625.19 X |
| 1,190,225 | 7/1916 | Ewen | 137/625.19 X |
| 1,250,918 | 12/1917 | McMichael | 137/625.19 X |
| 1,830,594 | 11/1931 | Crowe | 137/625.19 |
| 2,434,723 | 1/1948 | Shook | 73/863.71 |
| 2,592,371 | 4/1952 | Ackroyd | 137/625.19 |
| 3,236,207 | 2/1966 | Happel | 119/14.47 X |
| 3,282,651 | 11/1966 | Ferrari et al. | 137/625.19 X |
| 3,369,405 | 2/1968 | Galegar | 73/863.33 X |
| 3,459,176 | 8/1969 | Leonard | 128/760 |
| 3,476,518 | 11/1969 | Jungner | 73/864.16 X |
| 3,542,070 | 11/1970 | Sheeter | 137/625.19 |
| 4,088,025 | 5/1978 | Foster et al. | 73/863.33 |
| 4,100,805 | 7/1978 | Cossin | 73/863.31 |
| 4,288,206 | 9/1981 | Tigwell et al. | 73/863.31 X |
| 4,346,609 | 8/1982 | Diesel, II | 73/863.33 |

FOREIGN PATENT DOCUMENTS

| | | | |
|---|---|---|---|
| 24234 | 3/1919 | Denmark | 73/863.31 |
| 35695 | 3/1926 | Denmark | 73/863.31 |
| 728392 | 10/1942 | Fed. Rep. of Germany | 137/625.19 |
| 832252 | 2/1952 | Fed. Rep. of Germany | 137/625.19 |
| 653064 | 5/1951 | United Kingdom | 73/863.31 |
| 2053155 | 2/1981 | United Kingdom | 73/863.31 |

Primary Examiner—Gerald Goldberg
Assistant Examiner—Tom Noland
Attorney, Agent, or Firm—Cushman, Darby & Cushman

[57] ABSTRACT

A sampling device for obtaining a plurality of milk samples from the teats of a cow, the device comprising a body with sockets to receive the ends of tubes connected to teat cups, passages in the body connecting the sockets with individual sample cuvettes and a common valve member for opening or closing the passages between the sockets and the sample cuvettes. An overflow passage is provided upstream of the valve member for disposal of excess milk.

6 Claims, 5 Drawing Figures

BIOLOGICAL FLUID SAMPLER

This invention relates to a sampling device for use in sampling of biological fluids and in particular for sampling of milk specimens from the teats of a cow.

Hitherto the taking of milk samples from the teats of the udder of a cow has been on an individual basis or on a simultaneous basis such as in the Rapid Mastitis Test (RMT) or California Mastitis Test (CMT). In the latter test a sampling plate was utilized having four cup-like recesses or sockets which approximated the relative positions of the teats. The sampling plate was held on an inclined angle which was usually at 45° to the horizontal and milk samples were taken which ranged from 5 ml in volume to relatively large samples such as 20 ml. While this method was useful it was not appropriate for small volume analysis wherein samples of the order of 0.5 to 1.0 ml were required.

The taking of individual samples while useful for small volume analysis required the use of test tubes and pipettes and was considered to be relatively inefficient and time consuming.

It is therefore an object of the invention to provide a sampling device which alleviates the abovementioned disadvantages associated with the prior art.

The taking of milk samples from the teats of a cow is useful in that the four teats are classified as right rear (RR) left rear (LR) right front (RF) and left front (LF) and the sampling must be performed simultaneously to give an accurate picture of the degree of infection of a complaint such as mastitis. If all four teats give a positive analysis for the complaint then the degree of infection of course is much higher than a positive result given for one or two teats. Information as to which teat returns a positive result is also useful in determining the site of infection.

The sampling device of the invention includes:

a sampling block containing a plurality of sample passages;

connection means interposed between each sample passage and the associated sampling location of a body of an animal, and valve means for ensuring that flow of sample fluid in each sample passage occurs simultaneously; and collection means associated with each sample passage.

The invention is of most interest in the simultaneous sampling of milk from the teats of a cow as previously described. However, it will be appreciated that the sampling device of the invention may be used for the simultaneous sampling of a plurality of different samples of other biological fluids from the body of an animal such as blood samples.

The sampling block or plate is preferably formed from clear or transparent plastics material and for the sampling of milk from the teats of a cow it will contain four or more sample passages. Preferably each sample passage is of uniform diameter and is rectilinear with each other so that a row or line of sample passages are located in the sampling block. However, this is not essential and the sample passages may be staggered or arranged around the periphery of the sampling block if required. This latter situation is useful when each sample passage is provided with an individual valve unlike a common valve means as hereinafter described.

As stated above the valve means for the sake of convenience is suitably a common valve means between each sample passage and preferably includes a valve stem having a handle wherein the valve stem is located in a mating passage in the sampling block which is transverse to the longitudinal axes of each sample passage. The valve stem may also include a plurality of openings which may be aligned with a respective sample passage when in the open position so as to allow sample fluid to flow through each sample passage. Upon a rotation of the stem by the handle each opening may then be out of registry or alignment with its associated sample passage and hence the valve is then in the closed position.

Suitable retaining means may be provided for retaining the valve stem in position so that it is mounted within the sampling block and in one form this may comprise a spring surrounding an outward extension of the valve stem which projects laterally of the sampling block. There may be provided a collar or abutment on the outer extension of the valve stem which maintains the spring in a state of compression or tension between the abutment and the adjacent surface of the sampling block.

Preferably each sample passage is provided with an overflow port to allow excess sample fluid to be disposed of or drained away from the sample passage. Preferably each overflow port is oriented so that it projects downwardly at an angle relative to the longitudinal axis of its respective sample passage. The angle of each overflow port may range from 30° to 45° to the horizontal. The provision of overflow ports in each sampling passage is useful in that it facilitates the taking of small volumes of sample fluid by inhibiting sudden surges of fluid taking place through each sample passage and interfering with the taking of appropriate sample volumes by the collection means.

The collection means may comprise individual collection vessels such as test tubes releasably engageable with an associated sample passage. However, more preferably the collection means includes a plurality of collection vessels such as cuvettes mounted on a common stand or frame which is releasably attachable to the sampling block by clip means. Each cuvette in this embodiment may register with an associated sample passage.

The connection means suitably comprises connection tubes or hoses formed from flexible material such as PVC or rubber which at one end are attachable to a respective teat and at the other end engage in as associated sample passage in a interference fit relationship.

Reference may now be made to a preferred embodiment of the invention as shown in the attached drawings wherein.

Figure 1:
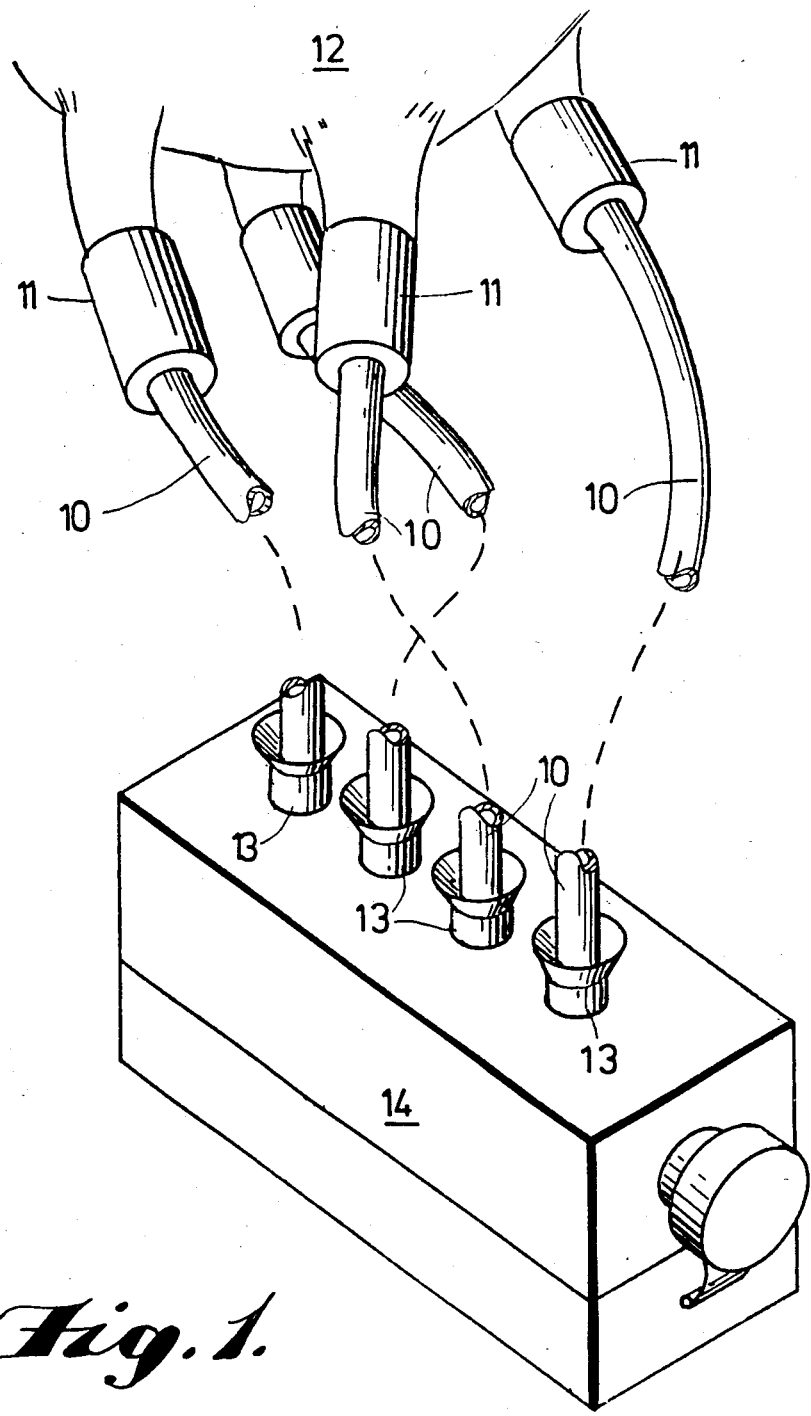
FIG. 1 is a perspective view of sampling apparatus constructed in accordance with the invention.

The apparatus as shown includes connection tubes 10 having attachment sleeves 11 for attachment to the teats of the udder 12 of a cow. There is also shown funnels 13, sample passages 13A of sampling block 14 and valve 15 comprising valve handle 16, abutment 17, valve stem 18 having openings 18A, abutment 19 and retaining spring 21 interposed between boss 20 and sampling block 14 on abutment 19. Each sample passage 13A may include an overflow port 24. Each passage 24 is parallel to each other and extends through a common face of block 14.

There is also shown collection stand 22 having cuvettes 23 mounted thereon for the collection of samples which is releasably attached to block 14 by clips 25.

There also may be provided a conductivity electrode (not shown) associated with each sample passage 13A. There also may be alarm means which is preferably of the visual type associated with each conductivity electrode which will be actuated when an increased conductivity value is attained which is a departure from the normal conductivity value.

The valve means may also be modified so as to provide for partial opening or closing of the sample passage if such is considered disirable.

The apparatus of the invention may also be modified for large volume analysis e.g. (10–20ml) if such is considered appropriate.

The sample of milk in its cuvette may then be analysed by appropriate means (e.g. the catalase or NAGase tests) so as to determine the presence of infection and also the level thereof in the animal being tested.

Figure 2:
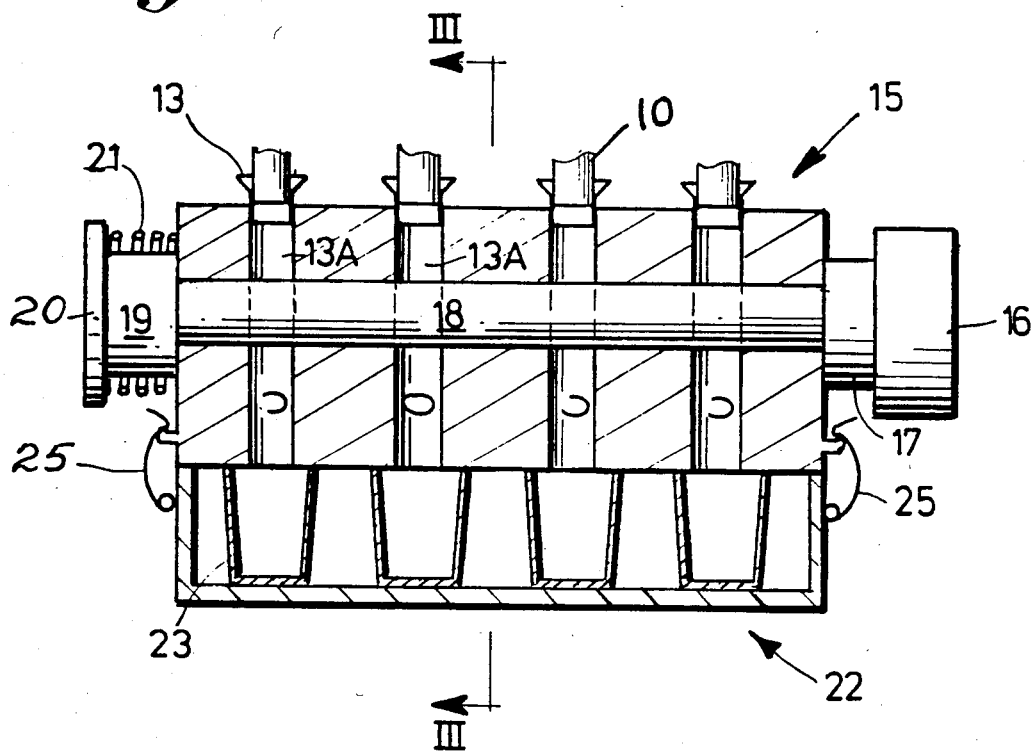
FIG. 2 is a perspective view of the apparatus shown in FIG. 1.
Figure 3:
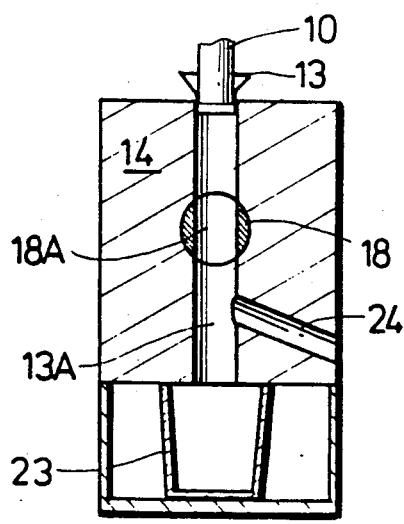
FIG. 3 is a sectional view through the apparatus of FIG. 2 taken on the line III—III.
Figure 4:
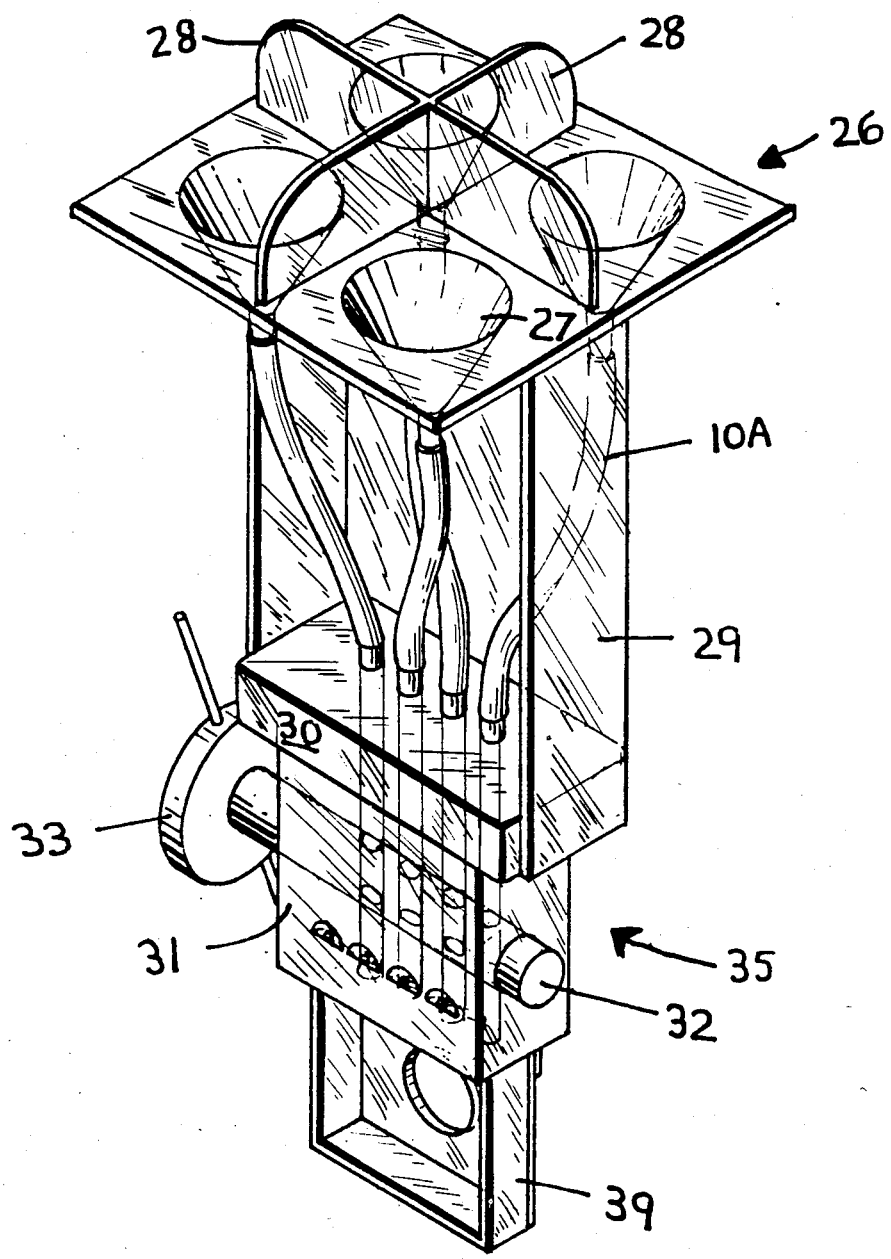
FIG. 4 is a perspective view of another type of sampling apparatus constructed in accordance with the invention.

In FIG. 4, the apparatus shown includes a teat engagement plate 26 having conical teat engaging sockets 27 and separating partitions 28. Flexible tubes 10A pass from the bottom part of sockets 27 to a sampling block 35 comprising upper portion 30 which is attached to plate 26 by end walls 29. The sampling block also includes a body part 31 having sample passages 36 and air bleeder holes 37 as shown. Valve stem 32 engages in body part 31 and has handle 33. The valve stem 32 engages with the sampling block 35 in a manner as described in FIGS. 1–3 and includes openings 38 similar to valve openings 18A previously described.

There is also shown cuvette stand 39 which is suitable for the mounting of cuvettes (not shown) directly below a respective sample passage 36. Air bleeder holes 37 facilitate milk running freely through passages 36 and avoid surface tension effects wherein the milk has a tendency to adhere to passages 36.

Figure 5:
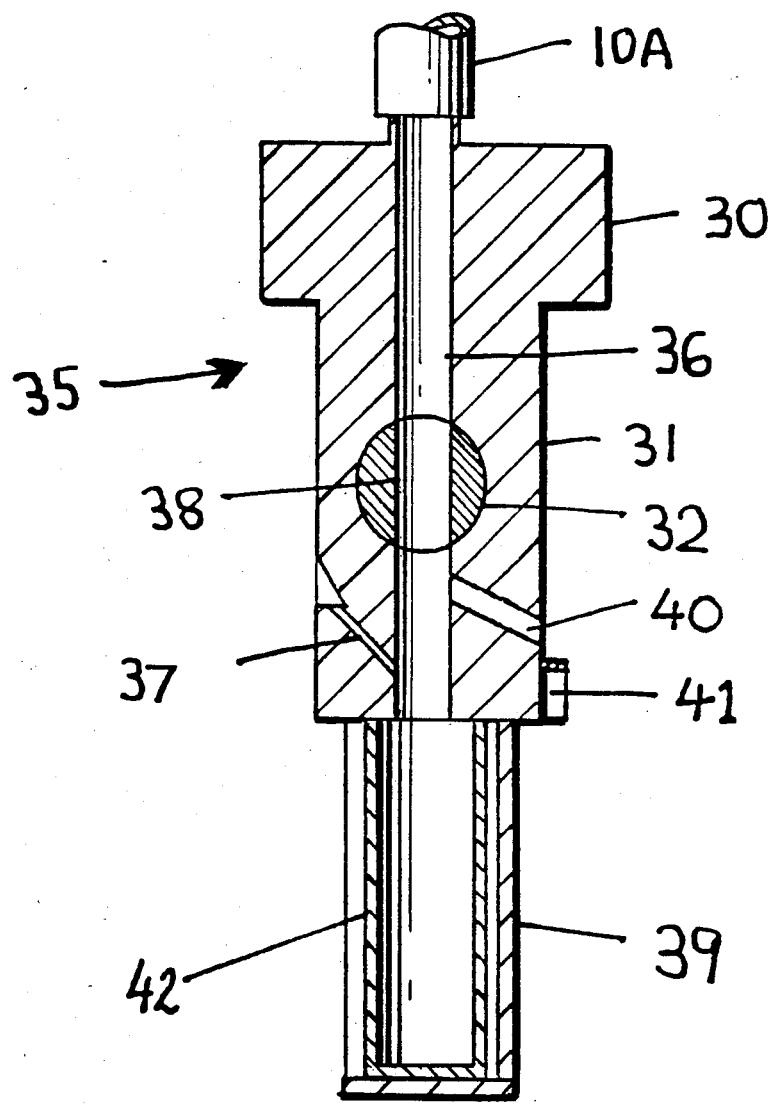
FIG. 5 is a sectional view through the sampling block of FIG. 4.

FIG. 5 shows a cross section through the sampling block 35 of FIG. 4. Immediately below the overflow passages 40 is a deflection flange 41 extending outwardly from body part 31 and sloping at an angle across the face thereof. This deflection flange 41 prevents contamination of samples in the cuvette 42 by excess milk flowing from the overflow passages 40.

We claim:

1. A sampling device for use in sampling of biological fluids such as milk including:
   a sampling block containing a plurality of sample passages, each sample passage being provided with an overflow port capable of draining away excess sample fluid from the sample passage;
   connection means interposed between each sample passage and an associated sampling location of a body of an animal; and
   valve means common for each sample passage for ensuring that flow of sample fluid in each sample passage occurs simultaneously, said common valve means including a valve stem located in a mating passage in the sampling block which is transverse to the axis of each sample passage and said valve stem having a plurality of openings wherein each opening may be aligned upon rotation of the valve stem with an associated sample passage when in the open position so as to allow sample fluid to flow through each sample passage; and
   collection means associated with each sample passage.

2. A sampling device as claimed in claim 1 wherein each sample passage is cylindrical in cross section and of uniform diameter and is rectilinear with each other so that a row of sample passages are located in the sampling block.

3. A sampling device as claimed in claim 1 wherein the orientation of each overflow port is such that it projects downwardly at an angle relative to the longitudinal axis of the adjacent sample passage.

4. A sampling device as claimed in claim 1 wherein the collection means includes a plurality of collection vessels mounted on a common stand or frame below the sampling block.

5. A sampling device as claimed in claim 4 wherein the common stand or frame is releasably attached to the sampling block.

6. A sampling device as claimed in claim 1 wherein the connection means includes connection tubes or hoses formed from flexible material which may at one end engage or be located adjacent a respective teat of a cow and at the other end engage with an associated sample passage.

* * * * *